United States Patent [19]
Shoher et al.

[11] Patent Number: 5,975,903
[45] Date of Patent: Nov. 2, 1999

[54] DENTAL IMPLANT AND IMPLANT SYSTEM

[76] Inventors: Edan C. Shoher, POB 2127, Herzeliya, Israel, 46702; Itzhak Shoher, PO Box 2127, Herzelia, Israel, 46722

[21] Appl. No.: 09/053,857

[22] Filed: Apr. 2, 1998

[51] Int. Cl.⁶ ........................................ A61C 8/00
[52] U.S. Cl. .......................... 433/173; 433/174
[58] Field of Search ................... 433/172, 173, 433/174, 175, 176

[56] References Cited

U.S. PATENT DOCUMENTS

| | | | |
|---|---|---|---|
| 4,348,183 | 9/1982 | Weissman | 433/174 |
| 4,622,010 | 11/1986 | Koch | 433/173 |
| 4,624,673 | 11/1986 | Meyer | 433/173 |
| 4,818,559 | 4/1989 | Hama et al. | 433/173 |
| 5,013,242 | 5/1991 | Prezmecky | 433/173 |
| 5,141,435 | 8/1992 | Lillard | 433/176 |
| 5,439,381 | 8/1995 | Cohen | 433/177 |

*Primary Examiner*—John J. Wilson
*Attorney, Agent, or Firm*—E. Lieberstein

[57] ABSTRACT

A dental implant and dental implant system which permits installation of the dental implant in shallow bone to increase anchorage of the dental implant in bone with the dental implant having an elongated shaft adapted for insertion within the alveolar cavity and a plurality of wings connected to the shaft along its length and extending radially outwardly therefrom to form a wing span of between at least 2 mm to 14 mm from the circumference of the shaft to anchor the shaft into bone and to facilitate bone osseointergration.

15 Claims, 12 Drawing Sheets

DENTAL IMPLANT AND IMPLANT SYSTEM

FIELD OF INVENTION

This invention relates to dental implants and to a dental implant system which permits installation of a dental implant in shallow bone, increases the anchorage of a dental implant in bone and to a technique to facilitate insertion without the need to form a surgical flap or to suture the incision.

BACKGROUND OF THE INVENTION

Conventional dental implants are designed as submergible structures to be inserted in a cavity in the alveolar bone of the jawbone in an edentulous region. In general, the conventional dental implant includes a main body implanted in the jawbone and a neck and head portion extending upwardly from the gingiva for attachment to a prosthesis. The implant body in current practice is configured in the form of a cylindrical shaft having an internally threaded cavity adapted to receive externally threaded abutment members which form the neck and head portions of the implant. Typically, a healing cap is threadably connected to the main body and following a reasonable healing period of between 3–6 months the healing cap is replaced by the abutment members which are fixedly attached to a prosthesis for forming an artificial tooth. It is at present considered essential for the implant length to be in excess of 10 mm and preferably between 13 mm–23 mm to assure clinical ossiointergration and satisfactory bone resorption during the healing period. This requires drilling a bore in the bone to a commensurate depth. Many potential problems are inherent in forming a hole through live bone to a depth of up to 20 or more millimeters without a risk of devitalization and necrosis of the bone. Moreover, the dentist must exercise great care in forming such a large insertion in the mandible or mandibular not to interfere with the maxillary sinus or the mandibular canal.

SUMMARY OF THE INVENTION

It has been discovered in accordance with the present invention that the implant vertical height can be reduced to substantially less than 10 mm provided the implant is securely anchored within the bone. Moreover, in accordance with the implant design of the present invention it is not essential to externally thread the implant.

The implant of the present invention has a preferred vertical height of less than 10 mm. This permits the implant to be used in cases of reduced vertical bone depth and to otherwise surgically insert the implant without causing interference with the maxillary sinus or the mandibular canal. An advantage of the implant design of the present invention is its use as a support for an attachment to a full denture in cases of shallow alveolar bone so as to provide the denture wearer with support comparable to that provided by a removable prothesis. In this case the implant height may be very short since its use will be only as point of attachment of the mandible to a full denture. It should however be understood that although the implant design of the present invention permits the implant to be shorter than 10 mm in length it may also be used with conventional implant configurations and lengths to improve anchoring of the implant to the bone.

The dental implant of the present invention comprises an elongated shaft adapted for insertion within the alveolar cavity and a plurality of wings connected to said shaft and extending outwardly from the circumference of said shaft to form a wing span of at least 1 mm and having a contoured shape for anchoring the shaft into surrounding bone.

The implant system for installation of a dental implant in accordance with the present invention comprises a dental implant having an elongated shaft adapted for insertion within the alveolar cavity, a plurality of wings connected to said shaft at a location along its length with said wings extending outwardly from the shaft a predetermined distance and having a wing span of at least 1 mm and a washer for holding soft tissue in place adjacent the shaft and above the wings of the embedded implant.

BRIEF DESCRIPTION OF THE DRAWINGS

Other features and advantages of the present invention will become apparent from the following detailed description of the invention when read in conjunction with the accompanying drawings of which.

DETAILED DESCRIPTION OF THE INVENTION

Contemporary dental implant surgery involves forming an incision along the alveolar ridge and elevating the mucoperiosteal flap of soft tissue toward the vestibule to expose cortical bone. The bone is then drilled through dense medullary bone to form a bore having a depth of at least 10 mm and typically up to 20 mm or more commensurate with the height of the dental implant. Although a flap procedure may also be used with the implant of the present invention an alternative procedure may be used in which a washer is place above a removed section of soft tissue which avoids forming a mucoperiosteal flap of soft tissue and eliminates the need to suture the tissue after the implant is surgically seated.

Common to the implant design of the present invention is a central body in the form of a shaft of any shape and cross sectional geometry with a plurality of members constituting wings radially extending outwardly therefrom. The implant forms a winged structure which is embedded in bone or in the socket of an extracted tooth preferably with the wings located at least 2 mm below the external surface of the original bone height to allow for bone growth between and over the wings. The wings may constitute the major portion of the implant especially where the implant will be inserted less than 10 mm into the bone, or used for additional anchorage of the shaft-like implant.

Figure 1A:
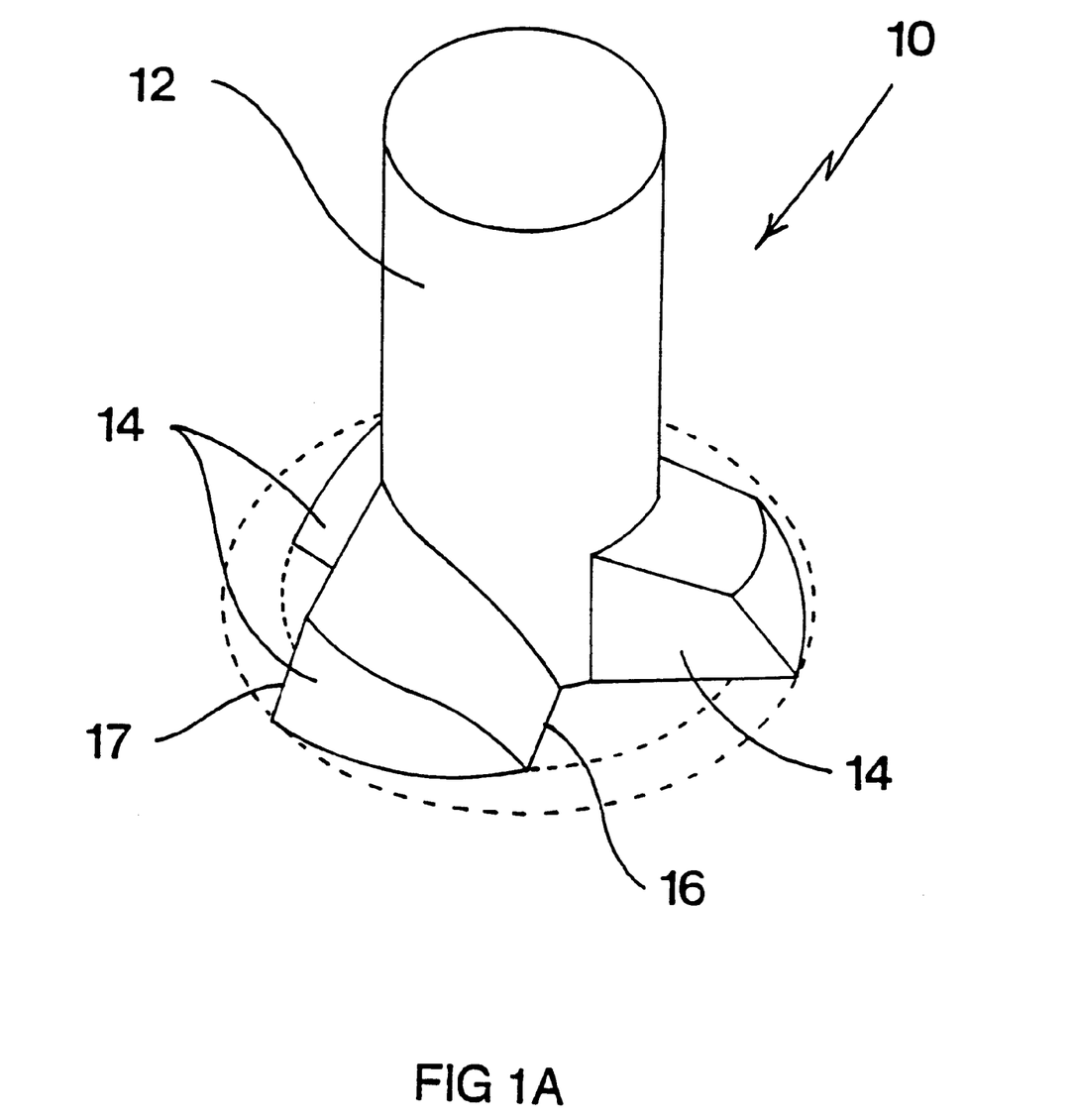
FIG. 1A is a perspective view of one embodiment of the implant of the present invention having a plurality of wings extending from a central shaft.
Figure 1B:
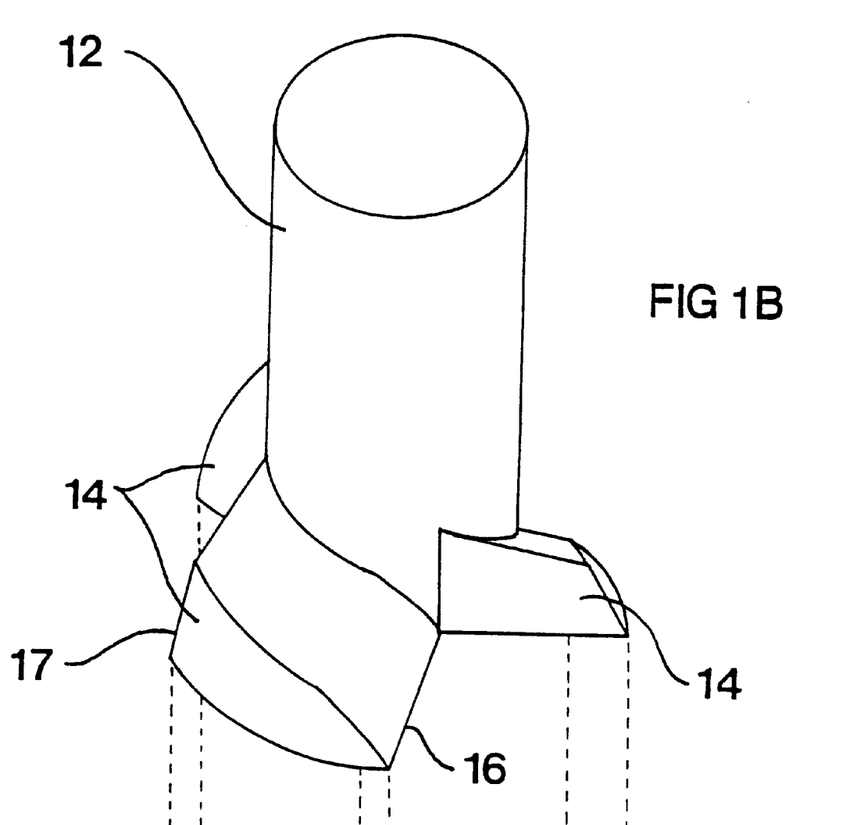
FIG. 1B is a perspective view similar to that of FIG. 1A.
Figure 1C:
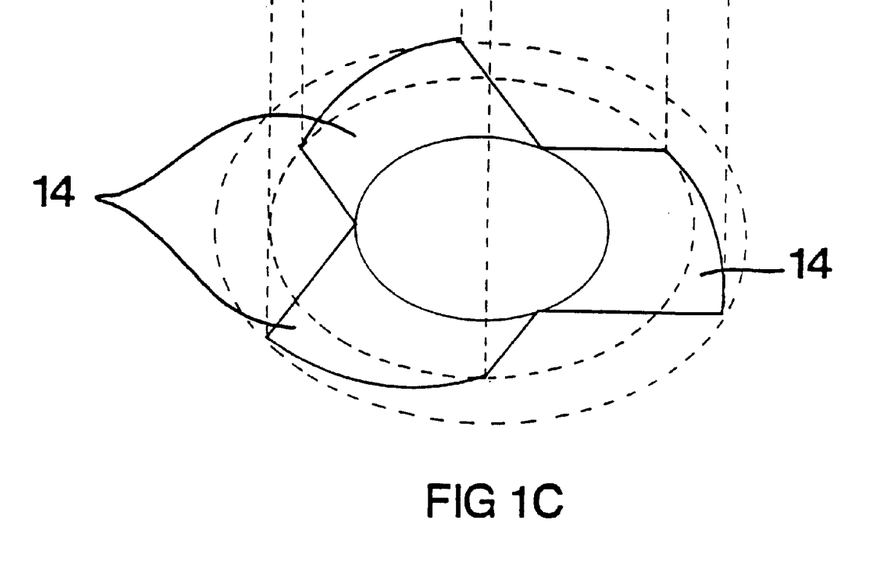
FIG. 1C is a bottom view of FIG. 1B.
Figure 4:
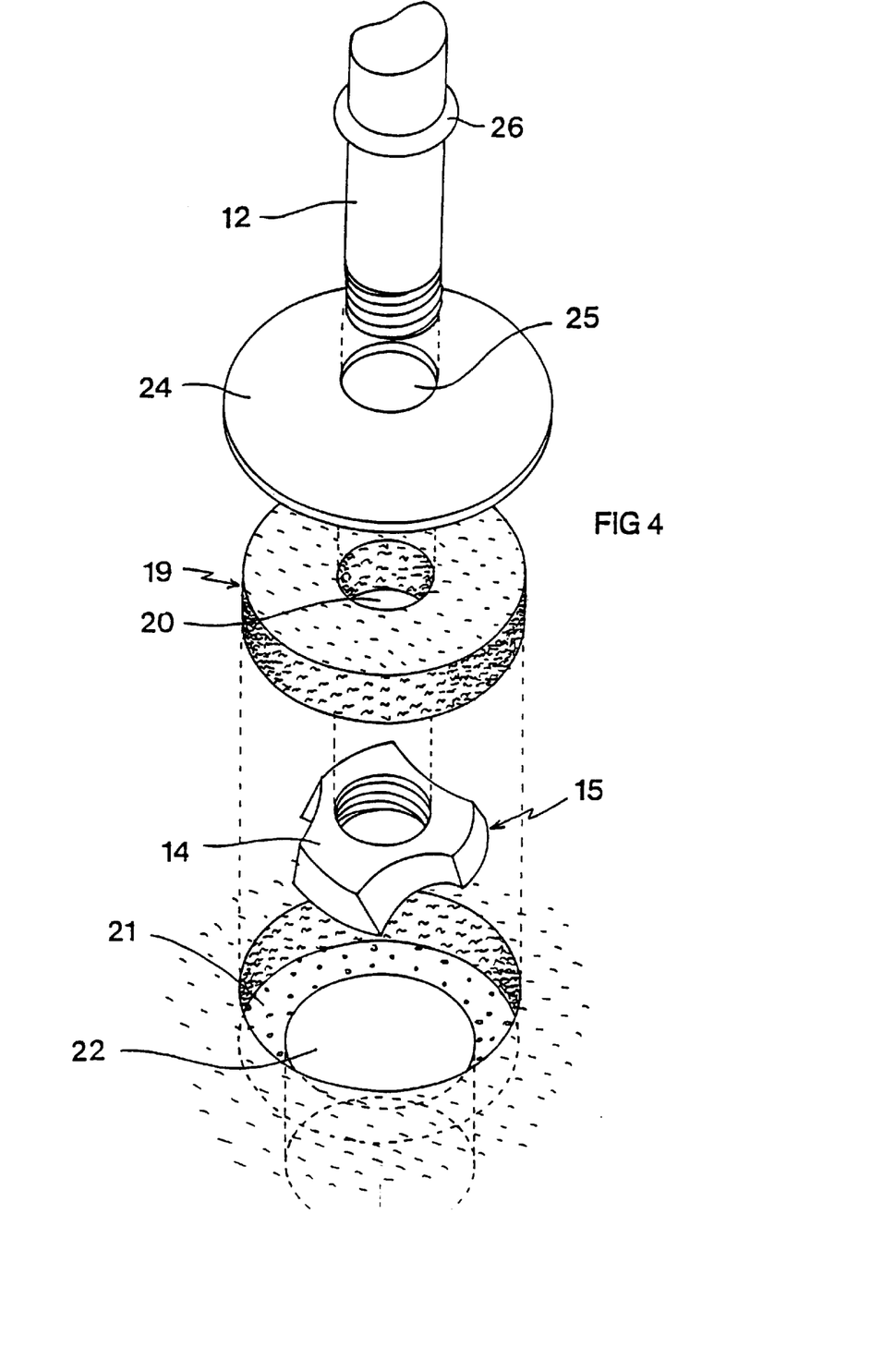
FIG. 4 is an exploded view of another embodiment of the implant and implant system for installation of the implant in accordance with the present invention.

One implant embodiment of the present invention is shown in FIGS. 1A–1E in which the implant 10 is of the type having a generally cylindrical body 12 defining an elongated shaft and a plurality of wings 14 extending outwardly from the central shaft 12. The wings 14 may each be separate from one another as shown in FIGS. 1A–1E and may be formed with the central shaft 12 as an integral body. Alternatively, the wings 14 may be interconnected to one another as an integrated body 15 separate from the shaft 12 as shown in FIGS. 2A–2B and FIG. 4. The separate body 15 of each wing 14 forms a three dimensional structure having a radial dimension extending from the elongated implant shaft 12, a circumferential dimension between the inner and outer edges 16 and 17 respectively and a thickness or height dimension with the circumferential dimension being substantially greater than the height dimension. In addition, the separate body 15 may be internally threaded (not shown) so that it may be threadably connected to the external threads 13 of the shaft 12 as shown in FIGS. 2A and 2B. The wings 14 radially extend from the central shaft 12 to form a circumferential wing span extending from the shaft 12 a radial distance of at least between about 2 mm to about 14 mm. The larger wing span is intended for cases of shallow bone and a wide alveolar ridge. The wings 14 should be spread apart to allow for sufficient open radial space between themselves such that at least 20% of the space circumscribed by the wings 14 will constitute void space. However, the wings 14 may be arranged in rows spaced apart vertically. Even in this case it is desirable for the wings in a given row to be spread apart such that at least 20% of the space circumscribed by the wings constitute void space.

Figure 1D:
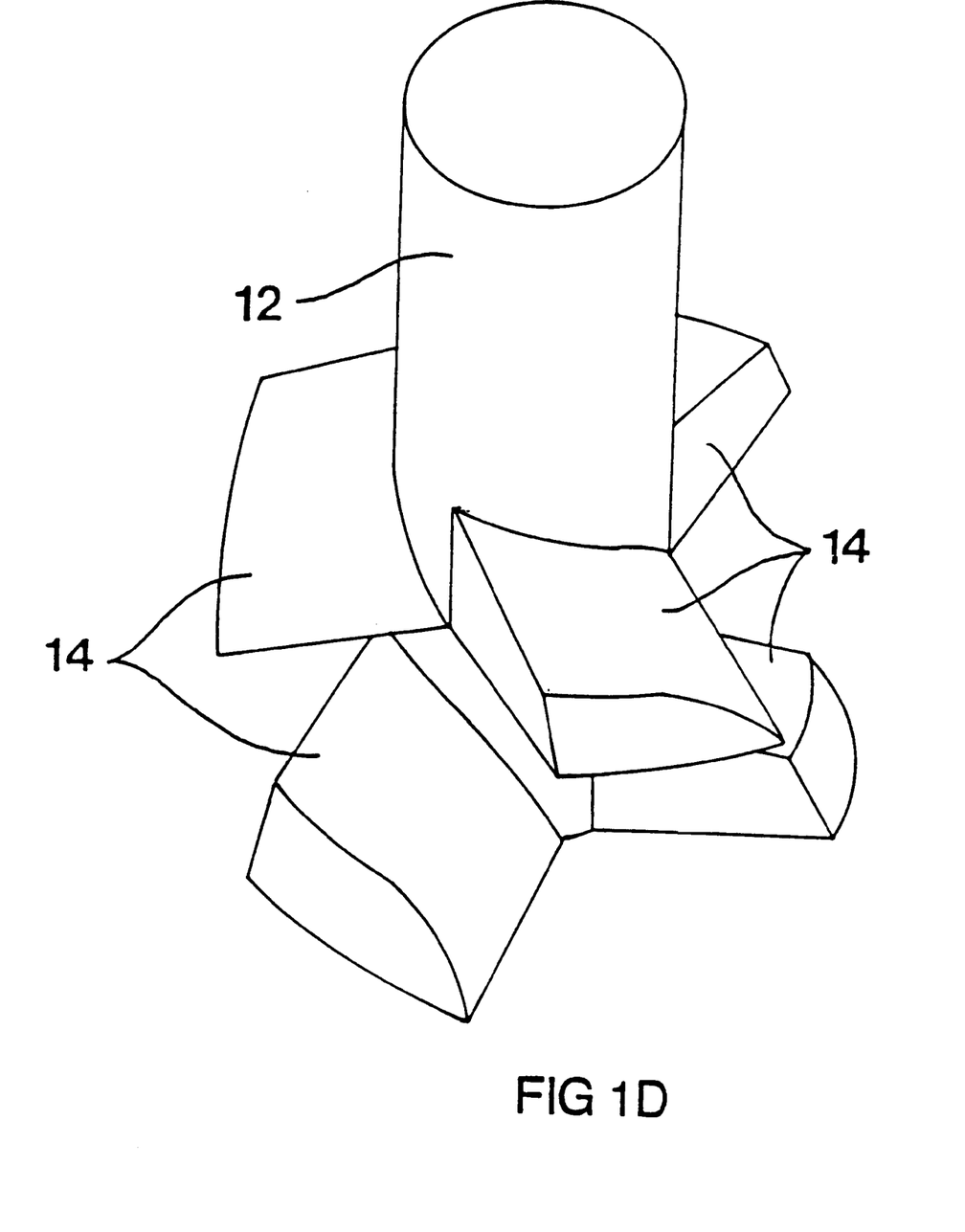
FIG. 1D is a perspective view of a variation of the implant of FIG. 1A showing two rows of a plurality of wings extending from a central shaft.
Figure 1E:
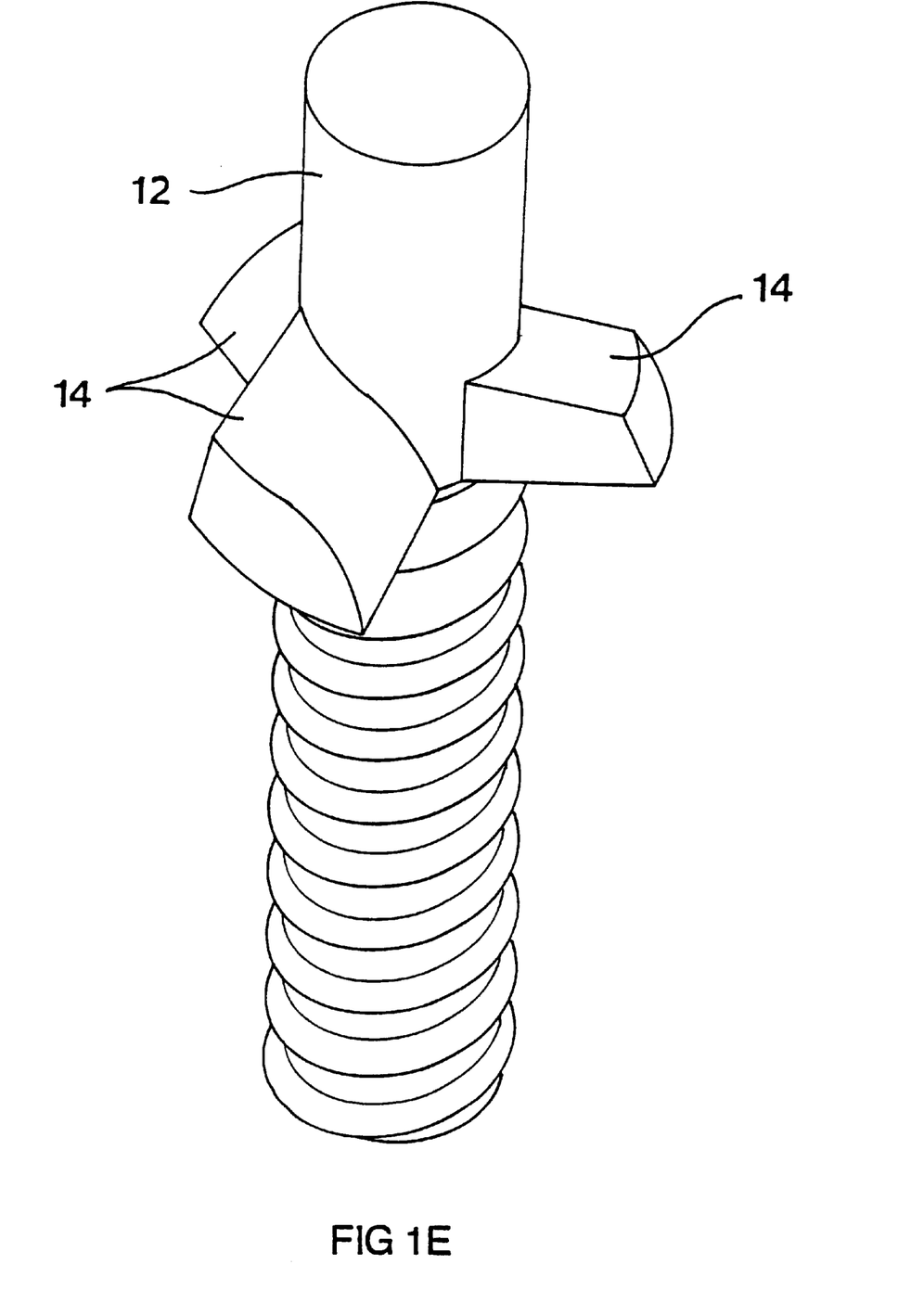
FIG. 1E is another variation of the implant of FIG. 1A in which the central shaft is externally threaded and the shaft extends apically to the wings.
Figure 2A:
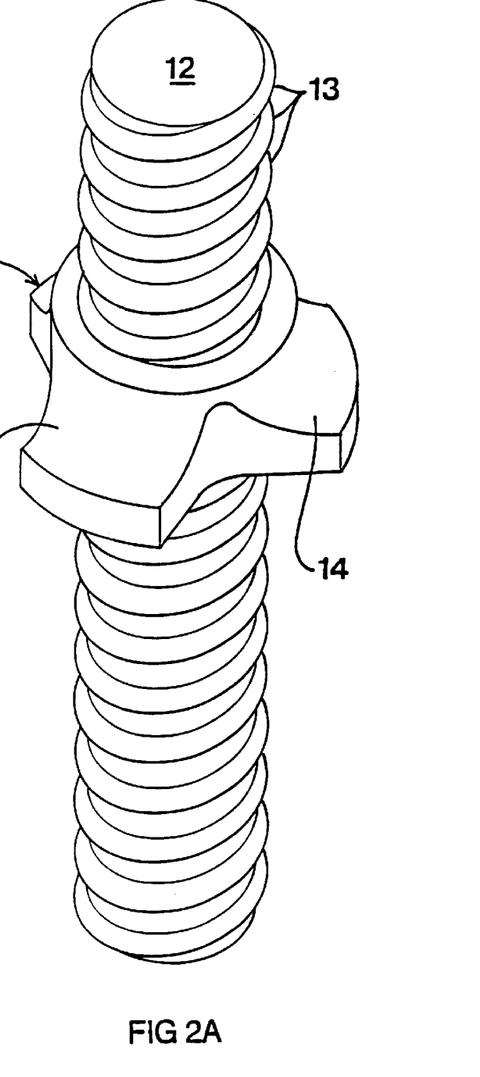
FIGS. 2A and 2B are perspective views of a second embodiment of the implant of the present invention in which the plurality of wings form an integral winged member which is threadably connected to the central shaft.
Figure 2B:
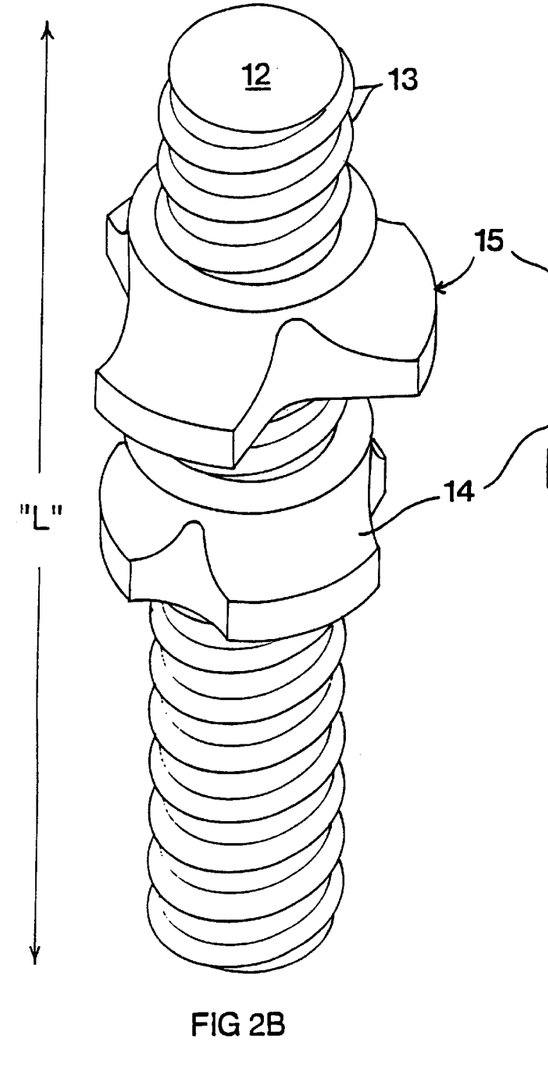
Figure 3A:
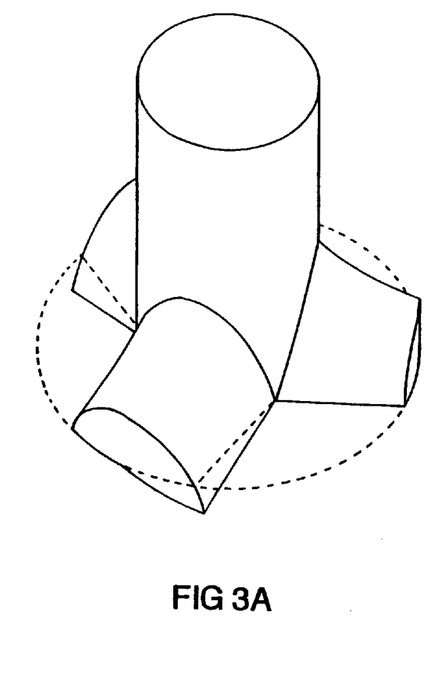
FIGS. 3A–3I are perspective views of the implant of the present invention similar to FIGS. 1A–1E and FIGS. 2A–2B showing variations in the shape of the wings.
Figure 3B:
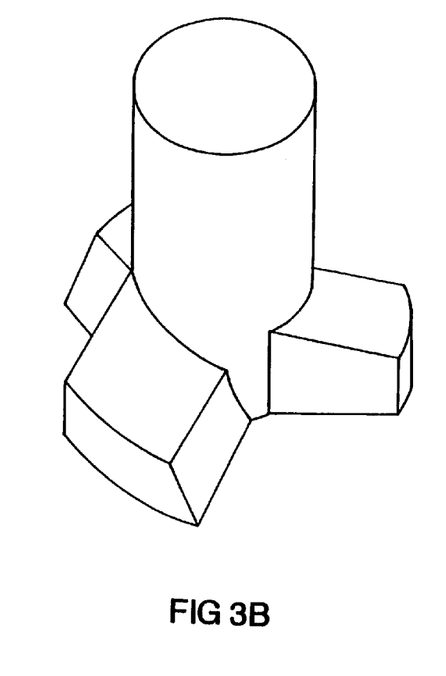
Figure 3C:
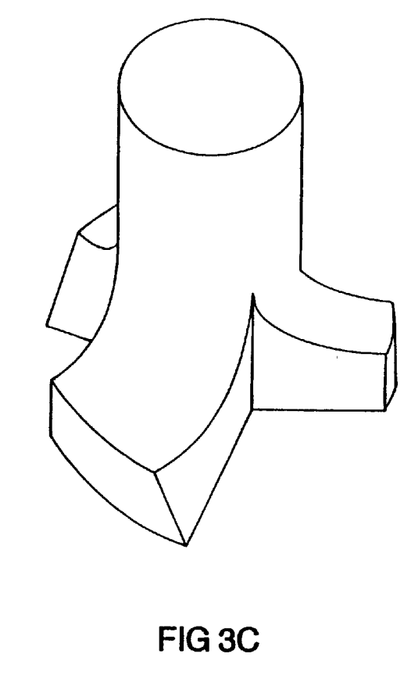
Figure 3D:
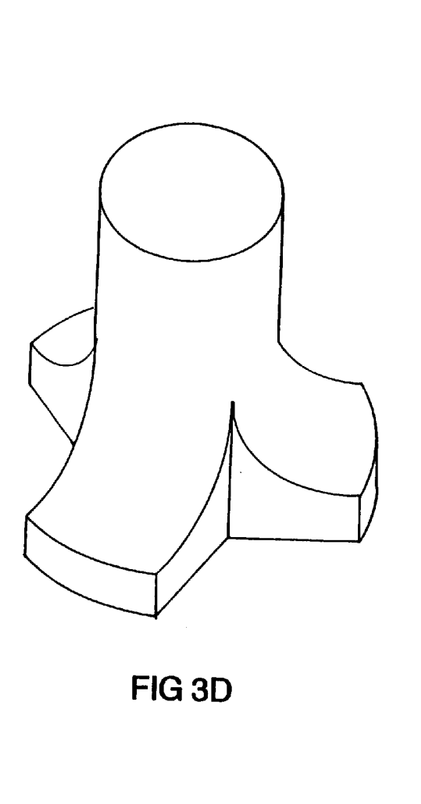
Figure 3E:
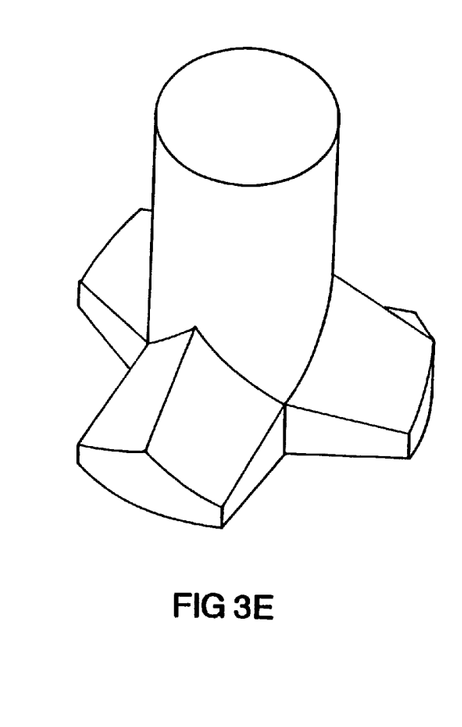
Figure 3F:
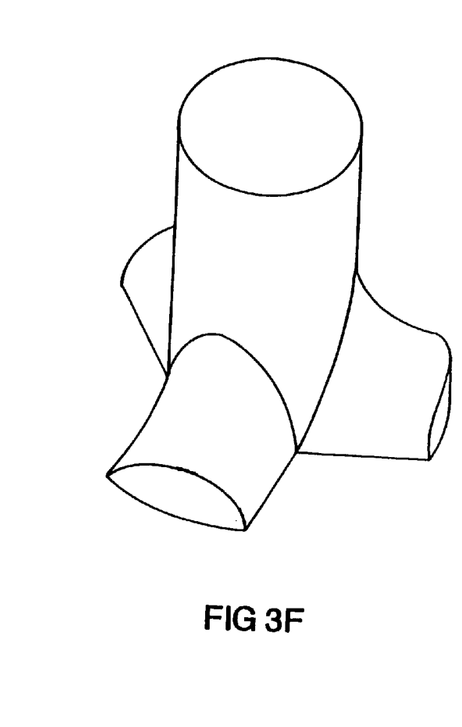
Figure 3G:
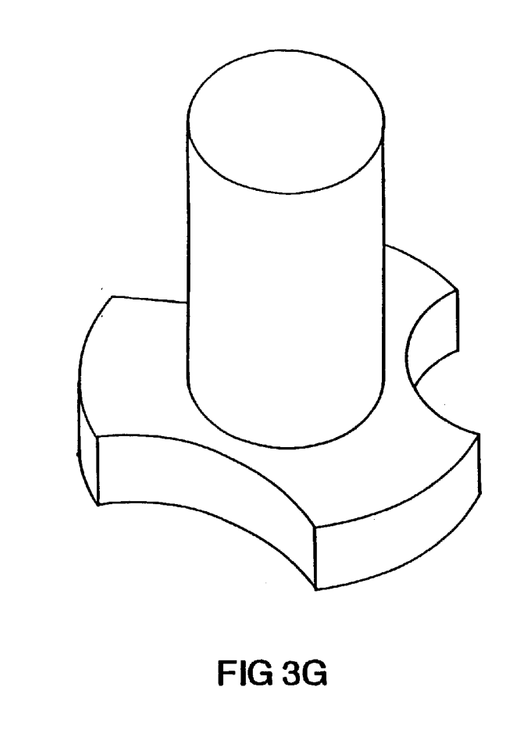
Figure 3H:
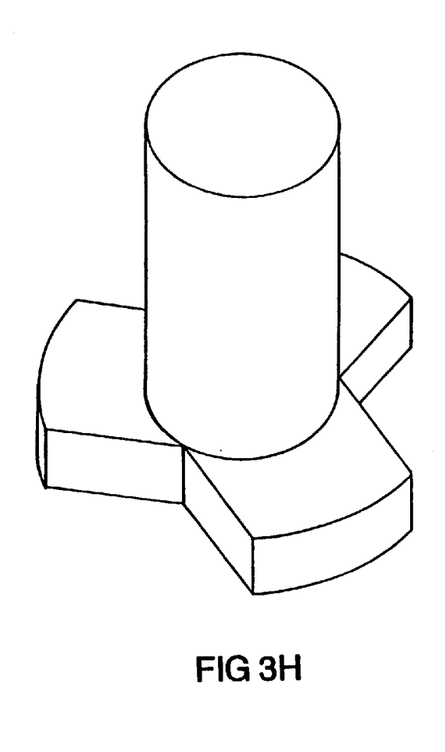
Figure 3I:
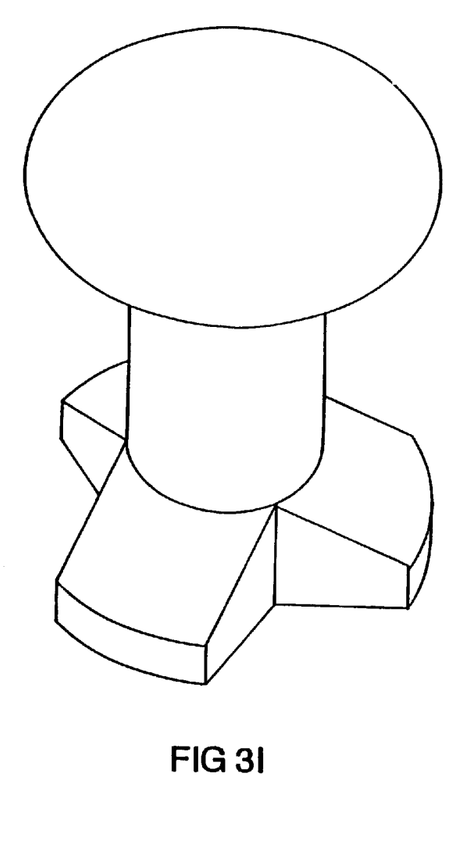

An arrangement of two rows of winged implants is shown in FIGS. 1D and 2B. It is not necessary for the rows of implants to be aligned relative to one another in any particular manner. Moreover the wing displacement or wing span of each row may be different from the wing displacement of other rows.

The thickness of the wings 14 may vary from about half a millimeter to 7 mm. The wings 14 may be of uniform thickness or of varying thickness. The shape of the wings 14 depend upon whether the winged implant will be inserted passively into a hole drilled into the bone or whether the winged implant will be actively inserted into bone by rotation of the implant. Active insertion requires the inner edge 16 of the wings 14 (assuming counterclockwise rotation) to form a thread in the bone. In FIGS. 1A and 1B the inner edge 16 of the wing 14 defines a cutting edge and is thinner than the outer or trailing edge 17 of the wing 14. Accordingly, the wing 14 is shaped to have a stronger incline or slope for self threading. In addition, the radial length of the inner cutting edge 16 is less than the radial length of the trailing or outer edge 17. This is more clearly evident form the bottom view 1C of the implant of FIG. 1B.

The central shaft 12 is preferably of the smallest diameter possible to allow for wider wings 14 and more bone to grow around and over the wings 14 to help keep them anchored. However the central shaft 12 may need to have an interior threaded cavity (not shown) at its proximal end to form an extension directed upwardly from the gingiva for attachment to an abutment ( not shown). All implants are adapted to be connected through abutments (not shown) to a dental prosthesis. Accordingly, the design of the central shaft 12 must accommodate the need to affix the implant 10 at its upper end to a prosthesis. Externally the shaft 12 may be of any shape including that of a cylindrical shape. The shaft 12 should be composed of a biocompatible material. The wings 14 may be of the same material as that of the shaft 12 or of a different biocompatible material. Among the materials of choice for the shaft 12 and wings 14 are titanium or precious metals or precious metal alloys.

Figure 5:
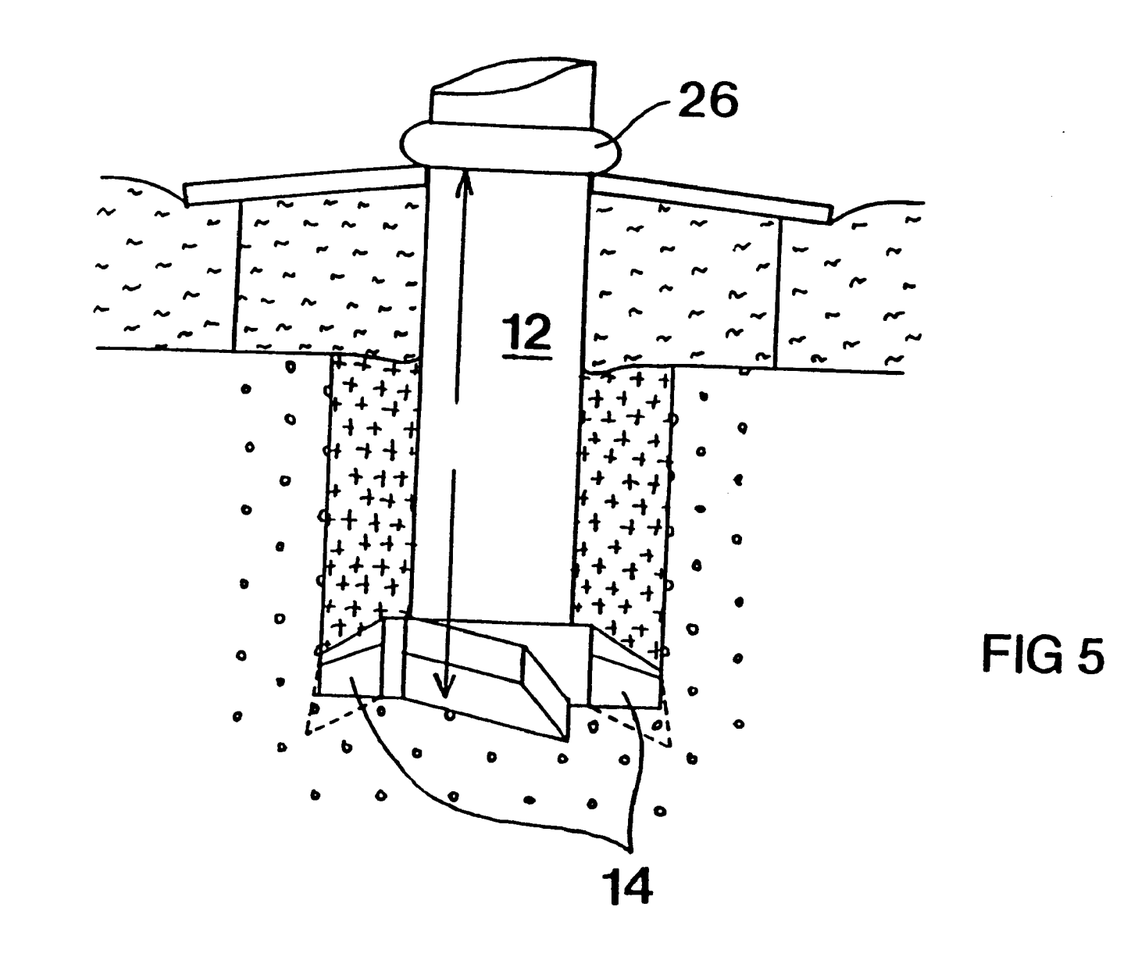
FIG. 5 is a cross sectional view of the assembled implant system of FIG. 4.

In accordance with the present invention the length "L" of the implant 10 (the implant length inserted in bone as shown e.g. in FIGS. 2 and 5) may be significantly shortened to a length not in excess of 10 mm although it may be used in conjunction with an implant of conventional length. In the present design the anchorage of the implant 10 in apposition to the bone is substantially increased by the use of the wings 14. The wings 14 may be engaged to the body 12 of the implant 10 at any location along its length "L". The preferred position of the wings 14 along the length "L" of the implant 10 also depends upon whether the implant 10 is to be actively or passively inserted into bone and how shallow the bone is. In the embodiment of FIG. 1A the wings 14 are shown located closer to the distal end of the implant 10 whereas in FIG. 1E the wings 14 are shown located closer to the proximal end of the implant 10. In FIGS. 2 A and 2B the position of the wings 14 are adjustable along the length "L" of the implant.

The winged member 15 has the appearance of a "nut" in FIG. 4. To install the implant 10 a section 19 of soft tissue is first removed from above the bone and a hole 20 punched through the section 19 of soft tissue. The diameter of the removed section 19 of soft tissue is preferably 2–3 mm wider than the hole 21 formed in the bone within which the implant is secured. The body 12 of the implant 10 is disassembled from the winged member 15 and/or from the attachment to the abutments which connect the body 12 to the prothesis so that it can be reassembled with the section of soft tissue 19 positioned between the wings 14 of member 15 and a washer 24. Pushing the cylindrical implant body 12 through the pierced hole 20 in the section 19 of soft tissue stretches the tissue sideways and helps keep it in place when put back into its original location. The hole 22 formed in the bone is sized to accommodate the diameter of the implant body 12 extending below the wings 14. The hole 21 is a counter bored hole which is larger than the hole 22 to accommodate the wings 14 of the member 15. The section 19 of soft tissue is reseated in the same position it occupied before its surgical removal. The washer 24 holds the section 19 of soft tissue in place adjacent adjoining tissue and above the edge of cortical bone circumferential to the drilled bone hole. This alleviates the need to suture the section 19 of soft tissue to surrounding tissue. Moreover the washer 24 can function as the healing cap or as part of a healing cap which is replaced after a healing period by abutment members fixedly attached to a prosthesis for forming an artificial tooth.

Figure 6:
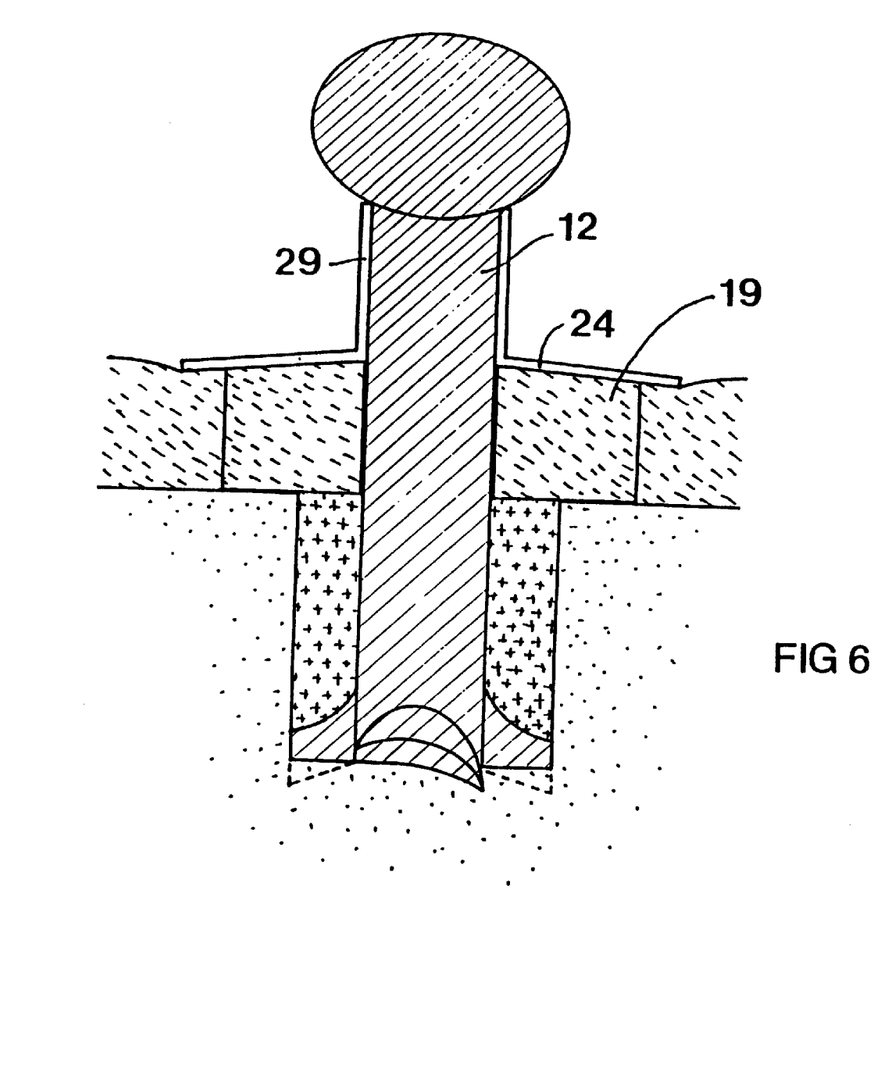
FIG. 6 is a cross sectional view of the assembled implant system using an L shaped washer for retaining soft tissue after insertion of the implant.
Figure 7A:
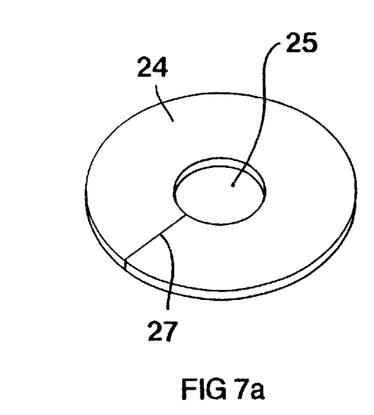
FIGS. 7a–7d illustrate in perspective variations in the washer design for the implant system of the present invention and FIGS. 8a–8d is a view in cross section corresponding to FIG. 7a–7d respectively.
Figure 7B:
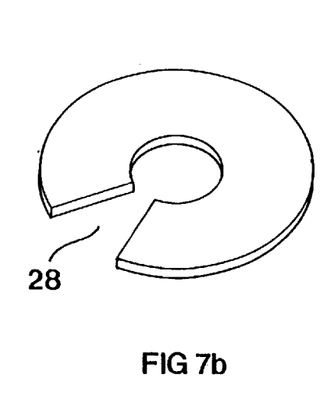
Figure 7C:
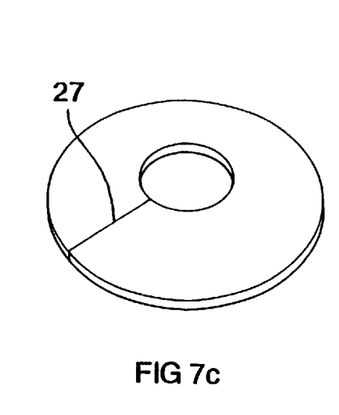
Figure 7D:
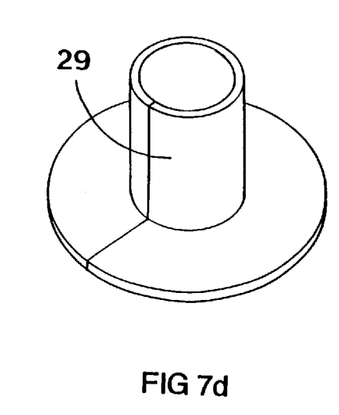
Figure 8A:
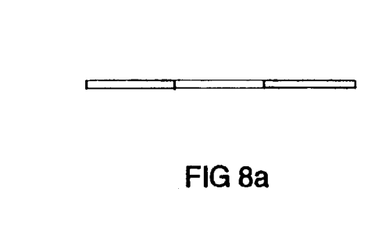
Figure 8B:
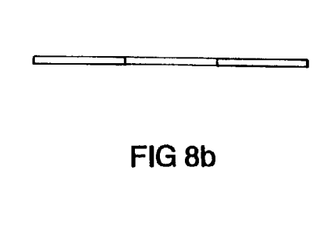
Figure 8C:
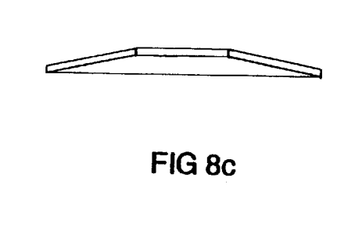
Figure 8D:
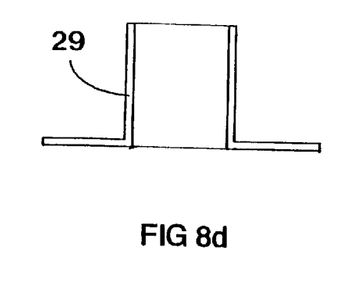

The washer 24 has a central opening 25 to facilitate assembly of the winged member 15 to the body 12 with the washer 24 clamping the section 19 of soft tissue in place. This procedure eliminates the need to suture the soft tissue and can accelerate the healing of the tissue. The washer 24 is, in turn, held in place by an annular ledge 26 formed around the body 12 of the implant 10 or by using an o-ring of biocompatible material to retain the washer 24. Alternatively, a groove (not shown) may be used in place of the annular ledge 26 to retain the washer 24 and/or the washer 24 may be connected to the implant body 12 by a screw (not shown) or other means to hold it in place. The configuration of the washer 24 may vary. A cylindrical washer 24 is shown FIGS. 4 and 5 and in FIGS. 7a–7c and 8a–8c respectively. The washer 24 preferably has a slit 27 extending radially from the central opening or an open space 28 formed by removing a radial section from its circumference. The washer 24 may be flat or bowed and if it is slitted it may overlap at the slitted opening. Alternatively the washer 24 may have a collar 29 extending upwardly to form an "L" shape washer in cross section . The "L" shaped washer 24 is shown in FIG. 6 and in FIGS. 7d and 8d respectively.

It should be understood that the shaft 12 and/or the wings 14 may have any desired surface characteristic and texture and may be surface treated with a hydroxyapatite composition to facilitate bone ossiointergration. A hydroxyapatite composition formed from bone chippings or other suitable materials known to enhance bone formation may also be used where void spaces are formed about the winged implant structure. Various commonly known implant attachments such as healing caps and other implant components may be used with the implant and implant system of this invention.

What I claim is:

1. A dental implant comprising an elongated shaft adapted for insertion within the alveolar cavity, a plurality of wings fixedly connected to said shaft at a specified location along its length with each wing extending radially outwardly from said shaft to form a three dimensional structure having a radial dimension, a circumferential dimension and a thickness or height dimension with the circumferential dimension being substantially greater than the height dimension and with each wing having a wing span of between at least 2 mm to 14 mm from the circumference of the shaft with the wings adapted to anchor the shaft into bone and to facilitate bone osseointegration.

2. A dental implant as defined in claim 1 wherein said wings and said shaft form an integral body.

3. A dental implant as defined in claim 1 wherein said wings are interconnected to one another for forming a member separate from said shaft.

4. A dental implant as defined in claim 3 wherein said member is threadably connected to said shaft.

5. A dental implant as defined in claim 1 wherein the wings have a contoured shape with at least one cutting face for active insertion into bone.

6. A dental implant as defined in claim 1 wherein said wings have a thickness in a range from about half a millimeter to 7 mm.

7. A dental implant as defined in claim 6 wherein said wings and shaft is composed of a material selected from the group consisting of titanium precious metals and alloys thereof.

8. A dental implant as defined in claim 7 wherein said wings and shaft are surface treated with a hydroxyapatite composition.

9. An implant system for installation of a dental implant within the alveolar cavity comprising a dental implant having an elongated shaft, a member composed of a plurality of wings connected to said shaft at a location along its length with said wings extending radially outwardly from the shaft to form a wing span of between at least 2 mm to 14 mm from the circumference of the shaft and a washer for holding a section of soft tissue adapted to be removed from above the cortical bone into which the implant is secured with the washer assembled to secure the section of soft tissue between the wings and the washer.

10. An implant system as defined in claim 9 wherein said washer has a central opening, is of a circular geometry and has a slit extending from its central opening.

11. An implant system as defined in claim 10 wherein said washer is bowed.

12. An implant system as defined in claim 10 wherein said washer extends upwardly forming an "L" in cross section.

13. An implant system as defined in claim 9 wherein said washer has a radially extending open space.

14. An implant system as defined in claim 9 wherein said washer forms the healing cap or a part of the healing cap for the implant system.

15. An implant system as defined in claim 9 further comprising retaining means for holding said washer in place.

* * * * *